(12) United States Patent
Macchi

(10) Patent No.: US 8,911,686 B2
(45) Date of Patent: Dec. 16, 2014

(54) SEPARATION DEVICE

(76) Inventor: Diana Elisa Macchi, Milan (IT)

( * ) Notice: Subject to any disclaimer, the term of this patent is extended or adjusted under 35 U.S.C. 154(b) by 415 days.

(21) Appl. No.: 13/039,463

(22) Filed: Mar. 3, 2011

(65) Prior Publication Data

US 2011/0215257 A1 Sep. 8, 2011

(30) Foreign Application Priority Data

Mar. 5, 2010 (IT) .............................. MI2010A0369

(51) Int. Cl.
*G01N 1/14* (2006.01)
*G01N 21/33* (2006.01)
*G01N 1/40* (2006.01)

(52) U.S. Cl.
CPC ...... *G01N 1/4077* (2013.01); *G01N 2001/4088* (2013.01)
USPC ......... 422/534; 73/64.56; 73/65.01; 73/53.01

(58) Field of Classification Search
CPC ............. G01N 1/00; G01N 1/58; G01N 1/14; G01N 21/33; G01N 1/4077; G01N 2001/4088
USPC ........ 422/534; 73/53.01, 64.56, 64.55, 65.01; 250/458.1
See application file for complete search history.

(56) References Cited

U.S. PATENT DOCUMENTS

| | | | | |
|---|---|---|---|---|
| 526,695 | A | * | 10/1894 | Emery ........................... 210/252 |
| 652,966 | A | * | 7/1900 | Jandus ........................... 210/332 |
| 3,352,197 | A | | 11/1967 | Porges et al. |
| 4,662,829 | A | * | 5/1987 | Nehring ........................ 417/395 |
| 4,786,420 | A | * | 11/1988 | Dalessandro ................. 210/791 |
| 4,827,760 | A | | 5/1989 | Saito |
| 4,861,725 | A | * | 8/1989 | Liau ........................... 435/293.2 |
| 5,160,444 | A | * | 11/1992 | McFarland .................... 210/805 |
| 5,528,368 | A | * | 6/1996 | Lewis et al. ................... 356/456 |
| 5,705,059 | A | * | 1/1998 | Miltenyi .................... 210/195.1 |
| 2007/0238169 | A1 | * | 10/2007 | Abilez et al. ................. 435/325 |

FOREIGN PATENT DOCUMENTS

| | | |
|---|---|---|
| WO | 98/32001 | 7/1998 |
| WO | 2004/103530 | 12/2004 |
| WO | 2008/012847 | 7/2006 |

OTHER PUBLICATIONS

Jeong, S. I.; Kwonb, J. H.; Limb, J. I.; Cho, S.-W.; Jung, Y.; Sung, W. J.; Kim, S. H.; Kim, Y. H.; Lee, Y. M.; Kim, B-Y.; Choi, C. Y.; Kim, S.-J. "Mechano-active tissue engineering of vascular smooth muscle using pulsatile perfusion bioreactors and elastic PLCL scaffolds," Biomaterials, 2005, 26, pp. 1405-1411.*
Said, M.D., T.M.; Agarwal, Ph.D., A.; Zborowski, Ph.D., M.; Grunewald, M.D., S.; Glander, M.D., Ph.D., H.-J.; Paasch, M.D., Ph.D., U. "Utility of Magnetic Cell Separation as a Molecular Sperm Preparation Technique," J. Androl. 2008, 29(2), pp. 134-142. Reference is labeled pp. 1-13.*
Gorczyca, W. "Cytometric analyses to distinguish death processes," Endocrine-Related Cancer, 1999, 6, pp. 17-19.*

(Continued)

*Primary Examiner* — Christine T Mui
(74) *Attorney, Agent, or Firm* — Shoemaker and Mattare

(57) ABSTRACT

A separation device for preparing biological samples for cytological, cytohistological and histological analysis includes a series of communicating chambers, means for moving a fluid through the chambers and one or more separating units for separating material contained in the fluid, wherein the separator units are arranged along the path of the fluid between the chambers.

10 Claims, 3 Drawing Sheets

(56) References Cited

OTHER PUBLICATIONS

Darzynkiewicz, Z.; Smolewski, P.; Bedner, E. "Use of flow and laser scanning cytometry to study mechanisms regulating cell cycle and controlling cell death," Hematol Oncol Clin N Am, 2002, 16, pp. 339-355.*

Miltenyi, S.; Muller, W.; Weichel, W.; Radbruch, A. "High Gradient Magnetic Cell Separation With MACS1," Cytometry, 1990, 11, pp. 231-238.*

Pokorny et al. "Ultraviolet-Visible Spectrophotometry in the Analysis of Lipid Oxidation," Analysis of Lipid Oxidation. Publication Date May 2005. 24 pages.*

* cited by examiner

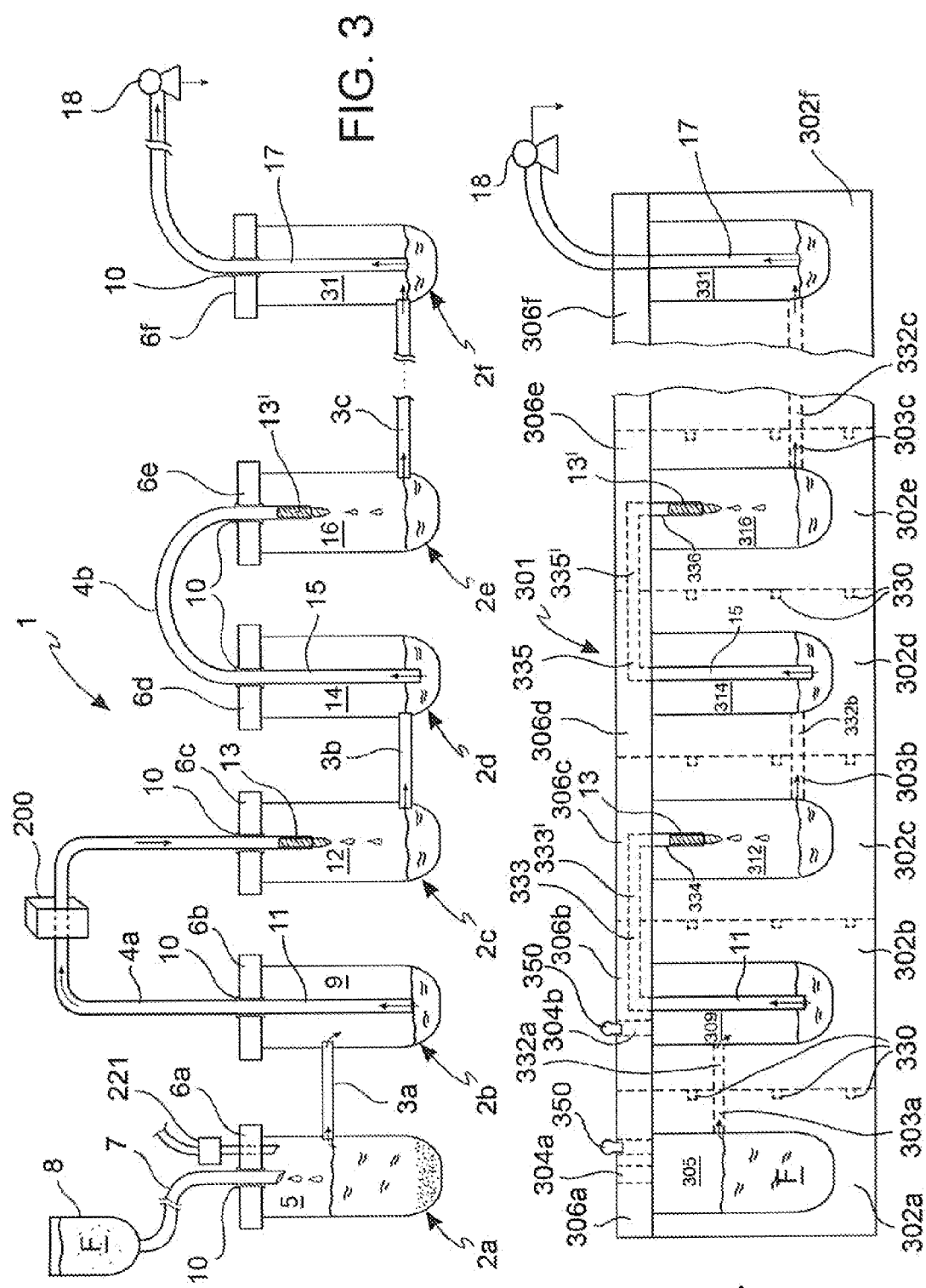

SEPARATION DEVICE

FIELD OF THE INVENTION

The present invention refers to a device for preparing some biological samples to be used in cytological, cytohistological and histological analysis.

STATE OF THE ART

It is known that the diagnostic cytology is the branch of pathological anatomy which aims at observing, with different detection instruments and methods, cells and/or cellular aggregates, obtained in any manner, arranged on a microscope slide, suitably fixated with the aim of identifying the altered cells and/or cellular groups and thus formulate a diagnostic hypothesis useful to the doctor to identify the pathology in course.

The diagnostic cytology applies various techniques aimed at valorising the material obtained in any manner from tissues and/or organs of subjects and prepared on microscope slides adapted to allow suitable study. The preparations follow the collection of organic material generally conducted through exfoliative methods (spontaneous urine, phlegm, etc), abrasive methods (pap-test, brushings, fixation, scraping of tissues and/or mucosa, washing), invasive techniques (various organic liquids, needle aspiration or FNAB, etc.) methods.

Furthermore, technically, the preparations are usually divided into:

direct preparations on microscope slides of the material collected according to any of the abovementioned techniques and suitably fixated according to the diagnostic needs (fixation at the air, fixation with alcoholic solutions, etc);

preparation of material in liquid phase after enriching through centrifugation;

preparation of material considered having poor cellularity with resuspension of the bottom of the centrifugate and thus cytocentrifugation directly on the microscope slide;

preparation by cytoinclusion of material, generally microfrustolated, previously enriched and concentrated on the bottom of a test tube by trapping the same through various techniques (agar, celloidine, thromboplastin, etc);

preparations by cytoinclusion of semi-solid material;

specific preparations such as suspensions in Saccomano fluid, suspension of materials obtained by abrasion and "millipore" and/or "nucleopore" treatment, suspension in means suitable for differential separation (Sephadex®) and others.

All illustrated methods, usually used in cytology laboratories, provide for numerous technical steps such as centrifugation, resuspension and cytocentrifugation, and inclusion of the residue bottom in the test tubes after centrifugation. These steps are necessary for recovering the study material in the abovementioned form specifically required by the particular type of study to be conducted and the relative working diagnosis inherent with the indication under analysis.

In particular, when the technician is dealing with a given method to be conducted on a biological sample, the technician is necessarily required to process the sample so as to recover the material in a well determined form so as to provide the preparation to the utmost. The optimisation of such operation requires a separation of the material of interest from what constitutes the overall of the collected material. In other words, for some particular and/or special analysis, the material to be prepared and analysed should be separated from anything that can alter the preparation result and, especially, the ensuing study in any manner whatsoever. In order to obtain this, the technician is forced to conduct often sensitive and complex operations such as several centrifugation and resuspension operations with the ensuing waste of time, work materials and with the risk on one hand of not accurately preserving the study material and on the other hand wasting considerable amount of said material. Furthermore, the centrifugations must be provided under determined and precise conditions depending on the type of preparation and study to be carried out.

The biological material subject of study is always rich with information and the object of the various processing techniques is to extract from the latter as much data as possible, useful for diagnosis and/or follow-up of the patient and relative ensuing therapeutic choices.

In some cases, it is necessary to subject the sample to various treatment and/or separation steps. In case of starting from a liquid sample (blood plasma, urine, exudate or other biological fluid), the separation of one or more cellular components is often indispensible before conducting the required analysis on the fluid. Given analysis and determinations may instead be conducted on the cellular material separated from the fluid, always with the aim of obtaining the largest amount of information as possible from the sample.

It would thus be desirable to have a device capable of facilitating such operation, both in terms of speed of execution and in terms of efficiency and safety of use.

SUMMARY OF THE INVENTION

The technical problem on which the present invention is based is thus that of providing a device capable of allowing reducing the steps of preparing the biological material that should be prepared for different treatments as much as possible simultaneously considerably increasing the separation efficiency as well as the quality and quantity of the biological material available for the specific preparation.

Such problem is overcome by a separation device as described and claimed below.

BRIEF DESCRIPTION OF THE DRAWINGS

Further characteristics and advantages of the present invention shall be more apparent from the following description of some embodiments, provided purely by way of non-limiting example, with reference to the figures wherein;

FIG. 3 represents a schematic view of a further variant of the device of FIG. 1;

FIG. 4 represents a schematic view of a different embodiment of the invention.

DETAILED DESCRIPTION OF THE INVENTION

The idea on which the present invention is based is that of providing a device capable of facilitating the preliminary operations of preparing a biological sample for processing with the various methods of the diagnostic cytology so as to standardise them without being exposed to the risk of losing or altering the material of the sample.

A crucial step in any diagnostic cytology method is the separation of the material of interest from the sample collected from a patient. Such step usually comprises a series of compulsory steps, such as the ones described previously with reference to the conventional methods, in which the biological sample is treated under given conditions depending on the type of study to be carried out. As known, each type of treatment (centrifugation, resuspension, cytocentrifugation, etc) requires use of apparatus, supports for samples and solutions which require calibration from time to time.

In order to simplify the sample centrifugation and washing operations, a separation device which—through simple operations—allows preparing the sample for the various analytical operations in a quick manner and with as less human intervention as possible, was designed.

In given embodiments, the device of the invention allows subjecting the sample, as it is or partly or fully treated, to some analytical determinations in line with the separation device.

In given embodiments, the device of the invention is structured to allow an easy and safe interchangeability of the elements that compose it and the modularity of the device itself.

Figure 1:
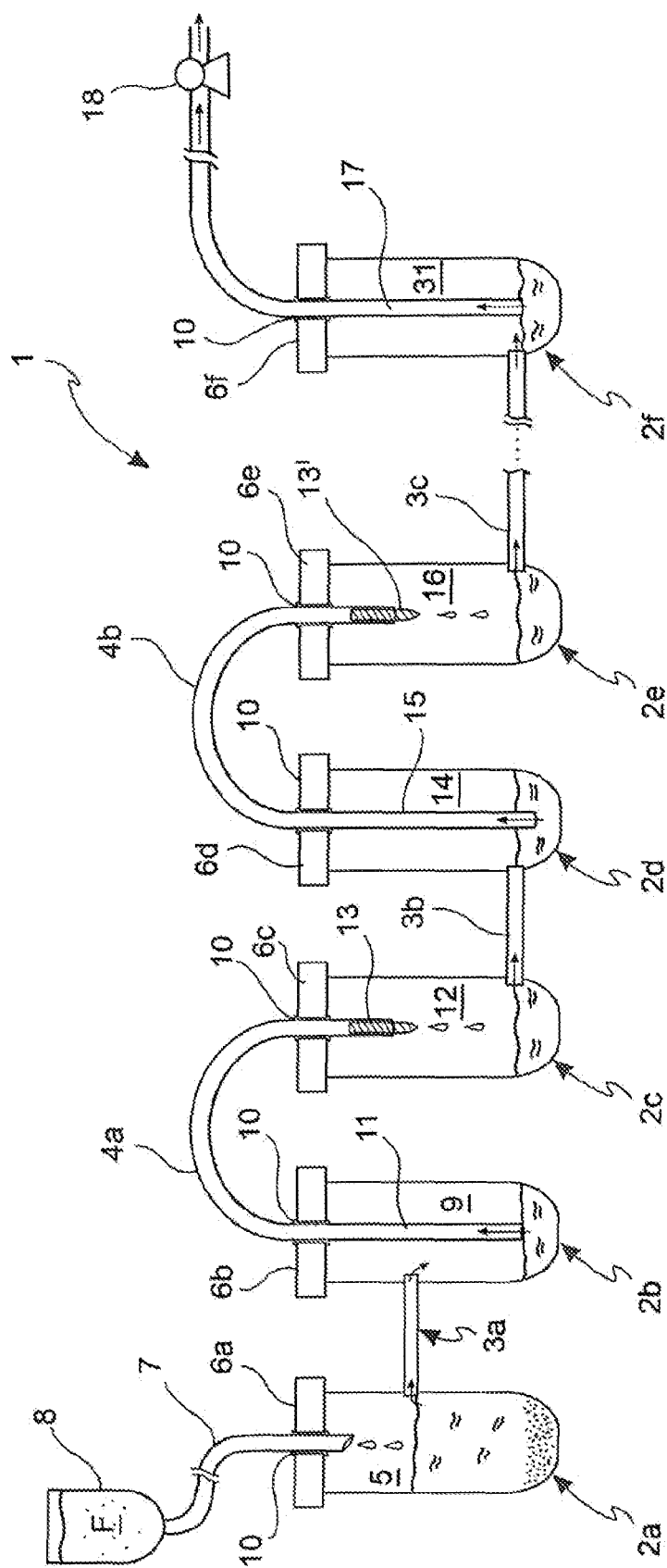
FIG. 1 represents a schematic view of an embodiment of the device of the invention.

With reference to FIG. 1, the separation device of the invention, indicated in its entirety with number 1, comprises a plurality of containers 2a, 2b, 2c, 2d, 2e, 2f connected in series in flow communication through suitable conduits 3a, 3b, 3c, 4a, 4b. The number of containers and relative conduits of communication shall be variable depending on the type of use and treatment required.

A first container 2a, for example a test tube or any other container that can be used for handling biological fluids, defines a decantation chamber 5 therein. Said first container 2a comprises a closure 6a having a through hole in which there is inserted the distal end of a tube 7. The tube 7 is in flow communication, through the opposite end, with a reservoir 8, typically a bag of the type used for medical purpose, containing the biological fluid F to be treated and analysed.

The closure 6a can be inserted on the container 2a by pressure or by screwing it. In such case, both the upper portion of the container 2a and the closure 6a shall be provided with complementary threads.

The tube 7 is inserted in the closure 6a in a sealed manner. For example, a sleeve gasket 10 may be provided for.

Within the first container 2a the biological fluid F is subjected to decantation so as to separate the coarse residue (part of the tissue, etc) which can be contained in the fluid on the bottom of the decantation chamber 5.

A first touch racking conduit 3a transfers the decanted fluid F into a second container 2b, within which there is defined a transfer chamber 9. The conduit 3a, which—in the embodiment of FIG. 1 is obtained by means of a tube—develops substantially horizontal or inclined towards the container 2b downstream and connects the containers 2a, 2b through opposite openings in the lateral walls thereof, serving as the touching means for the decanted fluid F. For such purpose, the conduit 3a is arranged at a level such as to allow a suitable decantation of the fluid F, preferably at the upper portion at half the height of the chamber 5.

The second container 2b comprises a closure 6b entirely analogous to the closure 6a of the first container 2a, in a through hole in which a suction tube 11 which continues, outside the container 2b, in a first transfer conduit 4a, is inserted. Usually the suction tube 11 and the transfer conduit 4a are in a single piece.

The transfer conduit 4a connects said second container 2b with a third container 2c through openings on the respective closures 6b, 6c of said containers. The closure 6c of the third container 2c is entirely analogous to the closures 6a, 6b described previously.

The third container 2c defines a collection chamber 12 therein. The transfer conduit 4a terminates within said collection chamber 12 and comprises, typically at the open end thereof, first separation means 13, adapted to separate a corpuscular component of the biological fluid F (for example, a cellular population, in single elements and/or in cellular aggregates and/or microfragments, or a protein or anything else depending on the mode of use) from the fluid.

In an embodiment, such separation means 13 are filtering means. A bag filter such as the one described in the patent application EP-A-2 052 231 in the name of Valenziano Susanna, whose description is incorporated herein for reference, may be advantageously used. Preferably, such filtering means have porosity P1 capable of withholding corpuscles of dimensions greater 50 micro-meters.

The third container 2c is in flow communication with a fourth container 2d through a second touch racking conduit 3b. Such conduit 3b develops with a substantially horizontal development and connects the lateral walls of the two containers to a lower level with respect to the end of the separation means 13 or the transfer conduit 4a, depending on which terminates lower.

The fourth container 2d is closed at the upper part by a closure 6d, analogous to those described previously, and internally delimits a transfer chamber 14.

A suction tube 15 is inserted into said transfer chamber 14, traverses the closure 6d and continues into a transfer conduit 4b, placing said fourth container 2d in flow communication with a fifth container 2e.

The container 2e is provided with a closure 6e, analogous to those described previously, which is traversed by said transfer conduit 4b. Within the container 2e a second collection chamber 16 is defined. The transfer conduit 4b terminates within said collection chamber 16 and comprises, typically at the lower end thereof, separation means 13'.

In an embodiment, said separation means 13' are filtering means, such as for example a bag filter, similar to those described regarding the separation means 13, but having a porosity P2 with lower diameter of the pores with respect to said porosity P1. Preferably, such porosity P2 shall be such to allow the separation of corpuscular material of dimensions comprised between 50 micro-meters and 10 micro-meters.

The container 2e is in flow communication with at least one further container 2f, through a touch racking conduit 3c which connects the lateral walls of the two containers to a level lower than the end of the separation means 13' or the transfer conduit 4b, depending on which terminates lower.

Also the container 2f comprises a chamber 31 and a closure 6f analogous to those described previously, through which a suction tube 17 is inserted.

In the embodiment shown in FIG. 1, the container 2f is the last of the series, hence the suction tube 17 serves as a conduit for evacuating the biological fluid F previously treated in the device of the invention. In such case, the suction tube 17 is operatively connected with means for moving said fluid which guarantee a flow of the biological fluid F through the device 1. Such movement means, in the shown embodiment, comprise vacuum pumping means 18.

The treated fluid F is then moved away through the tube 17 and then it is recovered downstream so as to be possibly subjected to further desired analysis.

It should be observed that the number of containers 2a, ... 2f may vary depending on the fluid F treatment needs, possibly being as few as four containers 2a, 2b, 2c, 2d and a single collection chamber 12, should the fluid require a single separation stage. Vice versa, the number of separation or treatment stages may also be greater than the one shown in the drawing, thus requiring providing a greater number of chambers in series.

In particular, it may be required to provide at least one further separation stage, for example using filters capable of separating corpuscular material with grain size comprised between 2 and 10 micro-meters, downstream of the second separation means 13' described above. Likewise, between the first separation means 13 and the second separation means 13' there may be provided a stage for separating particles with intermediate grain size.

When all the fluid F has been treated, the separation means 13, 13' shall be removed to recover the material withheld thereby, which may be possibly used for the desired clinical studies.

The means for moving the fluid may be arranged downstream of the device, as illustrated in the figures, or upstream. In this case they comprise pressurized pumping means.

Figure 2:
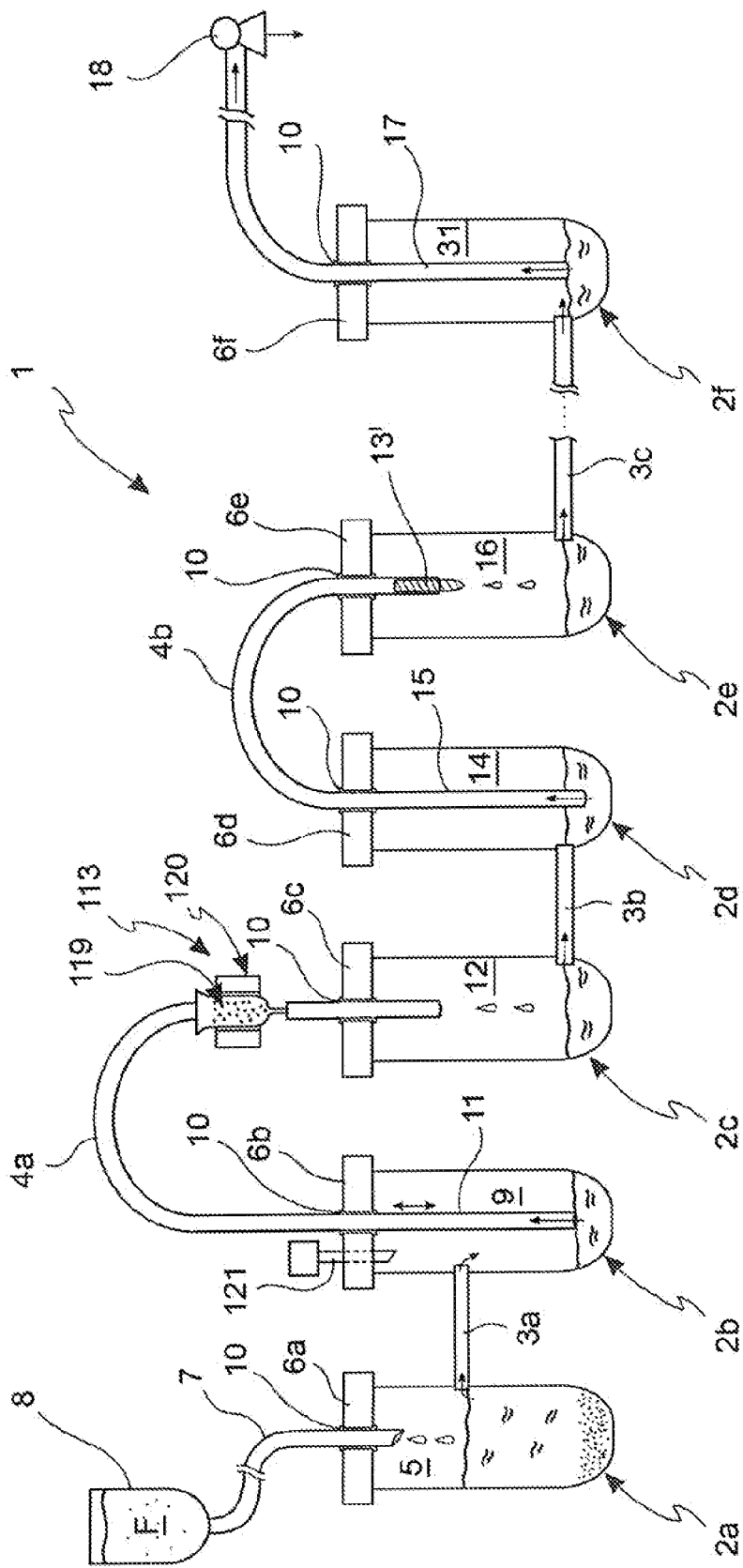
FIG. 2 represents a schematic view of a variant of the device of FIG. 1.

The embodiment of the invention device shown in FIG. 2 is similar to the one of FIG. 1, with the difference lying in that the stage of separating the corpuscular material from the fluid F between the first transfer chamber 9 and the first collection chamber 12 is actuated through separation means 113 arranged outside said first collection chamber 12 and comprising a separation system according to the MACCS® technology. Such technology, per se known and available in the market, provides for the advance marking of a cellular species intended to be separated through nanospheres made of superparamagnetic material (for example, through suitable antibodies functionalised with such nanospheres) and the subsequent passage of the fluid containing the cellular species thus functionalised through a column 119 containing a suitable porous filling material and arranged between the poles of a permanent magnet 120. The cellular species functionalised with the paramagnetic nanospheres is withheld in the column 119, while the fluid containing the remaining components passes. At the end of the operation, the column 119 is removed and eluted so as to recover the withheld cellular species. The paramagnetic nanospheres are biodegradable, hence a step for removing the marking is not required. Thus, this allows removing a cellular species regardless of the dimensions thereof, but according to the capacity of being functionalised, for example through a suitable antibody.

In FIG. 2, the closure 6b of the second container 2b has a second hole for the introduction of an adding means 121 —for example a tube that can be connected to a syringe or provided with a loading hopper—which can be used for introducing the paramagnetic nanospheres for marking the desired cells of the fluid F or for introducing other reagents or markers.

The embodiment of FIG. 2 also comprises separation means 13' comprising conventional filtering means, but such filtering means can also be replaced by the above-mentioned separation means 113 or that the first transfer conduit 4a comprises the separation means 13 for conventional filtration, while the separation means 113 described above are associated only to the second conduit 4b, or even that the device 1 comprises further separation means 13 or 113 downstream.

In FIG. 3 there is shown a further embodiment of the device of the invention, similar to the embodiment of FIG. 1, but with the difference that the transfer conduit 4a is intercepted by an analysis device 200 for the in line analysis of one or more components of the biological fluid F. Various types of analysis, such as for example spectroscopic analysis (for example, UV spectroscopy for determining DNA or RNA in solution), cells count ("Coulter counter") or flow cytofluorometer (for determining the dimensions and/or cellular form) can be provided for.

For example, the flow cytofluorometer provides for the use of light beam, typically laser light from Argon source, and the determination of the light diffused in the same direction of the incident light (Forward Scatter) or according to an angle of 90° (Side Scatter) through a suitable device for detecting and analyzing results. In the first case there is obtained information on the dimensions of the analysed cells, while in the second case there can be determined the roughness characteristics of the cellular surface and the number of organelles present in the cell. Possibly, the analysed sample can be treated with various fluorochromes free or conjugated with suitable monoclonal anti-bodies, so as to highlight the presence of specific cellular components such as proteins (fluorescein isothiocyanate) nucleic acids (propidium iodide) and lipids (Nile Red) or the enzymatic activity of esterase, peroxidase and peptidase. The fluorochromes can be conjugated to nucleotide probes for identifying DNA or RNA sequences.

The cellular components of the biological fluid F can be analysed as they are or in lysate form. In this case, the fluid F may be pre-treated with a suitable lysing agent, typically a lysing buffer.

For such purpose, the device of the invention may provide for means 221 for adding reagents such as lysing agents, fluorochromes or other marking agents. The adding means 221 are typically constituted by a tube which places one of the containers 2a, 2b in flow communication upstream of the analysis device 220 with the external or directly with a source of said reagents.

In FIG. 4 a further embodiment of the invention is shown, in which the device 301 comprises a plurality of modular elements 302a, 302b, 302c, 302d, 302e, 302f connectable in series through suitable coupling means 330. Each of said modular elements 302a, . . . 302f comprises a chamber 305, 309, 312, 314, 316, 331 for the decantation, the transfer or the collection of a biological fluid F, depending on the case, and respective closure plates 306a, 306b, 306c, 306d, 306e, 306f.

The first modular element 302a comprises a decantation chamber 305 and communicates with the exterior through at least one channel 304a which traverses the thickness of the respective closure plate 306a, so as to be connected with a bag or another container of a biological fluid F to be treated. One or more further channels 304a may be provided for supplying reagents, markers or another material, according to needs.

From the lateral wall of the decantation chamber 305 there originates a touch racking channel 303a which continues in a channel 332a which traverses the lateral wall of the second modular element 302b so as to transfer the decanted fluid F in the transfer chamber 309 of said second modular element 302b. The channel 303a, 332a is arranged at a level such as to allow a suitable decantation of the fluid F, preferably at the upper portion at half the height of the chamber 305.

The second modular element 302b comprises a suction tube 11 which continues, inside the corresponding closure plate 306b, in a transfer channel 333 which forms a substantially right-angled elbow. The transfer channel 333 continues, inside the closure plate 306c of the third modular element 302c, in a transfer channel 333' having a substantially mirror-like development, which connects said second modular element 302b with a third modular element 302c.

The closure plate 306b of the modular element 302b may comprise a channel 304b which places the chamber 309 in communication with the exterior, for supplying reagents, markers or other material.

Both the channel 304b and the channel 304a serve as means for adding said reagents, markers or other material and, if not used, they can be closed by suitable caps 350.

The third modular element 302c defines a collection chamber 312 therein. The transfer channel 333' terminates within said collection chamber 312 with a tube 334 which comprises first separation means 13, adapted to separate a corpuscular component of the biological fluid F (for example, a cellular population, in single elements and/or in cellular aggregates and/or microfragments, or a protein or anything else depending on the mode of use) from the fluid.

In an embodiment, such separation means 13 are filtering means. A bag filter such as the one described in the patent application EP-A-2 052 231 in the name of Valenziano Susanna, whose description is incorporated herein for reference, may be advantageously used. Preferably, such filtering means have porosity P1 capable of withholding corpuscles of dimensions greater 50 micro-meters.

The third modular element 302c is in flow communication with a fourth modular element 302d through a touch racking channel 303b which continues in a channel 332b which traverses the lateral wall of the fourth modular element 302d so as to transfer the fluid F in the transfer chamber 314 of said fourth modular element 302d. Such conduit 303b, 332b develops with a substantially horizontal development and connects the lateral walls of the two modular elements to a lower level with respect to the end of the separation means 13 or of the tube 334, depending on which terminates lower.

The fourth modular element 302d internally delimits a transfer chamber 314. A suction tube 15 is inserted into said transfer chamber 314 and continues in a transfer channel 335 obtained in the body of the closure plate 306d and which forms a substantially right-angled elbow. The transfer channel 335 continues, within the closure plate 306e of the fifth modular element 302e, in a transfer channel 335' with a substantially mirror-like development, which connects said fourth modular element 302d with said fifth modular element 302e.

The modular element 302e defines a collection chamber 316 therein. The transfer channel 335' terminates within said collection chamber 316 with a tube 336 and comprises separation means 13'.

In an embodiment, said separation means 13' are filtering means, such as for example a bag filter, similar to those described regarding the separation means 13, but having porosity P2 with smaller diameter of the pores with respect to said porosity P1. Preferably, such porosity P2 shall be such as to allow the separation of corpuscular material having dimension comprised between 50 micro-meters and 10 micro-meters.

The modular element 302e is in flow communication with at least one further modular element 302f, through a touch racking conduit 303c which continues in a channel 332c and connects the lateral walls of the two modular elements to a lower level with respect to the end of the separation means 13' or the tube 336, depending on which terminates lower.

Also the container 302f comprises a suction tube 17. In the embodiment shown in FIG. 4, the modular element 302f is the last of the series, hence the suction tube 17 serves as a conduit for evacuating the biological fluid F that has been treated in the device of the invention and collected in the chamber 331 of such modular element 302f. In such case, the suction tube 17 is operatively connected with vacuum pumping means 18 which guarantee a flow of the biological fluid F through the device 301.

The treated fluid F is then moved away through the tube 17 and it is then recovered downstream so as to be possibly subjected to the desired analysis.

It should be observed that the number of containers 302a, . . . 302f may vary depending on the fluid F treatment needs, possibly being as few as four containers 302a, 302b, 302c, 302d and a single collection chamber 312, should the fluid require a single separation stage. Vice versa, the number of separation or treatment stages may also be greater than the one shown in the drawing, thus requiring providing a greater number of chambers in series.

The device 1, 301 according to the invention may be made of any material suitable for the described applications, such as plastic, metal or glass. The dimensions of the containers 2a, . . . 2f or of the modular elements 302a, . . . 302f shall depend on the amount of fluid to be treated, but it shall be generally such to allow the use in an analysis laboratory.

From the description above, it can be observed that the handling of the filtered/washed material is advantageously simple and applicable to any type of preparation provided for by the diagnostic cytology, as indicated in the introductory part of the present description and with a possible use for histological material (e.g. VABRA, TURV, etc) using a bag filter suitable in terms of porosity according to the dimension of the tissue fractions to be withheld.

Furthermore, the separation device of the invention allows obtaining various types of separation in a single passage, both by filtration and according to various methods, as well as an in-line analysis which may provide some indications to the pathologist.

Moreover, the inventive device can be adapted to standardized methods, thus satisfying a long felt need in the state of the art.

Obviously, the described device may be subjected—by a man skilled in the art—to various modifications all falling within the scope of protection of the claims that follow.

It may be observed that the filtration/separation device described previously may also advantageously be applied to other fields of the art such as botany for the separation for example of cells from culture media, studies in the mineralogy sector for separating powders or other elements, in the wine industry for separating sediments or impurities and similar applications.

Furthermore, it may also be provided for sterile sets, previously prepared, that may be directly positioned in line with respect to drainage pipes exiting from the body of the patient, also bedridden, and instantaneously perform some evaluations through detection systems of the calorimetric type for each step, to be defined from time to time depending on the clinical data and the ensuing working diagnoses.

I claim:

1. A device for separating solid matter from a biological fluid, said device comprising
a plurality of modular elements which can be interconnected in series, each of said modular elements comprising a body having an open-topped chamber formed therein and a horizontal racking channel extending from said chamber through a side wall of the body, adjacent modules being placed with their racking channels in alignment, so that the respective chambers are in fluid communication with one another via said racking channels,
a like plurality of closure plates, one disposed on top of each of said modular elements so as to close the chamber thereof, each of said closure plates having a transfer channel formed therein, said transfer channel having one end communicating with said chamber and a second end extending through a side of the closure plate, whereby adjacent closure plates may be placed with their transfer channels in alignment, so that the respective chambers closed by said cover plates are in fluid communication with one another via said transfer channels,
a pump for moving a fluid containing the matter to be separated through said chambers via said racking channels and transfer channels, one or more filters for separating said matter from said fluid, as it flows between said chambers, and coupling means for connecting said modular elements together, wherein said channels are entirely contained within said modular elements and said closure plates.

2. Device according to claim 1, further comprising one or more analysis devices arranged along the path of said fluid between said chambers for analyzing matter contained in said fluid, said analysis devices being selected from the group consisting of a UV spectrograph, a cell counter and a flow cytofluorimeter.

3. Device according to claim 1, wherein said pump is arranged upstream or downstream of said chambers.

4. Device according to claim 1, wherein said pump is downstream of said chambers and comprise vacuum pumping means.

5. Device according to claim 1, further comprising at least one first decantation chamber upstream of said series of modular elements.

6. Device according to claim 5, wherein said at least one first decantation chamber is in flow communication with a first transfer chamber through a touch racking conduit or channel.

7. Device according to claim 6, wherein said touch racking conduit or channel has a substantially horizontal or inclined development towards said downstream transfer chamber and it is arranged at a level such as to allow a suitable decantation of the fluid.

8. Device according to claim 5, further comprising a last transfer chamber in flow communication with an external suction tube for drawing fluid through the device.

9. Device according to claim 1, comprising means for adding reagents, markers or dyes in said chambers.

10. Device according to claim 7, wherein said touch racking conduit or channel is arranged above half the height of said decantation chamber.

* * * * *